United States Patent
Hu

(10) Patent No.: US 9,061,978 B1
(45) Date of Patent: Jun. 23, 2015

(54) PROCESS FOR THE PRODUCTION OF ETHIONIC ACID

(71) Applicant: Songzhou Hu, Princeton, NJ (US)

(72) Inventor: Songzhou Hu, Princeton, NJ (US)

( * ) Notice: Subject to any disclaimer, the term of this patent is extended or adjusted under 35 U.S.C. 154(b) by 0 days.

(21) Appl. No.: 14/120,045

(22) Filed: Apr. 18, 2014

(51) Int. Cl.
*C07C 305/00* (2006.01)
*C07C 313/12* (2006.01)

(52) U.S. Cl.
CPC .................................. *C07C 313/12* (2013.01)

(58) Field of Classification Search
USPC .......................................................... 558/34
See application file for complete search history.

(56) References Cited

U.S. PATENT DOCUMENTS

| 1,913,794 A | 6/1933 | Daimler et al. |
| 2,634,287 A | 4/1953 | Fincke |
| 3,637,793 A | 1/1972 | van Gysel et al. |

FOREIGN PATENT DOCUMENTS

CN 202151566 2/2012

OTHER PUBLICATIONS

D.S. Breslow et al, J. Am. Chem. Soc., 1954, vol. 76, pp. 5361-5363.

*Primary Examiner* — Kristin Vajda

(57) ABSTRACT

The present invention discloses a process for the production of ethionic acid by reacting ethanol with sulfur trioxide in a molar ratio of 1:2 at a temperature from 40 to 100° C. in a falling film reactor while cooling the reactor with a cooling means.

8 Claims, No Drawings

PROCESS FOR THE PRODUCTION OF ETHIONIC ACID

TECHNICAL FIELD

The present invention relates to a process for producing ethionic acid, and in particular, to an improved process of producing ethionic acid, which comprises reacting ethanol and sulfur trioxide in a molar ratio of 1:2 in a falling film reactor while cooling the reactor with a cooling means.

DESCRIPTION OF THE INVENTION

Ethionic acid is an important intermediate for the production of alkali isethionate, alkali vinylsulfonate, and taurine. This acid has previously been prepared from ethanol and sulfur trioxide by three methods according to the following reaction schemes:

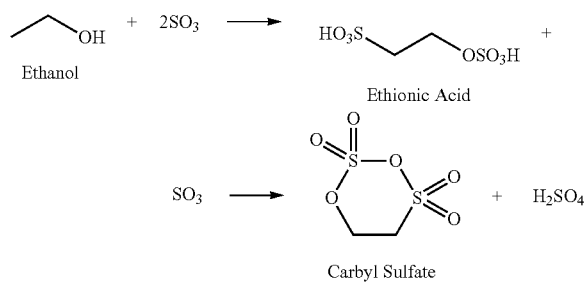

The first method relates to a process using liquid sulfur dioxide as reaction solvent. U.S. Pat. No. 1,913,794 discloses a method for preparing ethionic acid by reacting ethanol and pure sulfur trioxide in liquid sulfur dioxide. Both ethanol and sulfur trioxide are first dissolved in liquid dioxide, and then the sulfur trioxide solution is run into the ethanol solution while the reaction temperature is kept at the boiling point of liquid sulfur dioxide. The reaction heat is removed from the boiling of liquid sulfur dioxide. Quantitative yield of ethionic acid is obtained when the molar ratio of sulfur trioxide to ethanol is kept at 2:1.

U.S. Pat. No. 2,634,287 describes a continuous process of carrying out the reaction of sulfur trioxide and ethanol in liquid sulfur dioxide. According to this process, ethanol and sulfur trioxide are separately dissolved in liquid sulfur dioxide. The solutions are pumped and intimately mixed in a nozzle of relatively short length to complete the sulfonation. The liberated heat causes sulfur dioxide to vaporize within the nozzle and the product is obtained as a liquid residue. The vaporized sulfur dioxide may be compressed and liquefied to liquid sulfur dioxide for reuse in the process.

The disadvantage of this method lies in the use of sulfur dioxide as a reaction medium. Sulfur dioxide, which is toxic and pungent, must be recovered and recompressed into liquid form for the reuse, which represents a major operational expense. In addition, only pure sulfur trioxide can be used in the process. The use of pure sulfur trioxide is economically disadvantageous, since pure sulfur trioxide is much more costly than the contact gas produced in the sulfuric acid process The second method relates to a process for the direct sulfonation of ethanol with gaseous sulfur trioxide. A two stage process is described by Breslow et al (J. Am. Chem. Soc., 1954, Vol 76, pp 5361-5363). First, ethanol is reacted with the first mole of sulfur trioxide at a lower temperature of 0-5° C., then with the second mole of sulfur trioxide at a higher temperature of 50-70° C. Ethionic acid is obtained as a viscous, pale amber liquid. This two stage process is difficult to implement on an industrial scale, since the reaction heat from the exothermic sulfonation is inherently difficult to remove in the first stage at a temperature of 0-5° C.

CN 202151566 discloses a liquid film process for the reaction of alcohol with sulfur trioxide in a single stage. The reaction heat is removed in an external heat exchanger. As an example, ethanol is successfully reacted with pure sulfur trioxide to yield ethionic acid. However, only pure sulfur trioxide can be used as sulfonating agent in the device, which is economically disadvantageous.

The third method, disclosed in U.S. Pat. No. 3,637,793, relates to a process for preparing ethionic acid by reacting ethanol with sulfur trioxide in a molar proportion of 1:2 by use of ethionic acid as a reaction medium. The process can be carried out in any stirred reactor and in a specially designed constant level vessel, which is equipped with pump, heat exchanger, and Raschig ring column. Ethanol is introduced below the surface level and the sulfur trioxide above the level of the reaction medium. The reaction yield is practically quantitative and the reaction temperature is moderate at 40 to 100° C. Both pure sulfur trioxide and sulfur trioxide diluted with other inert gases can be used in the process.

When pure sulfur trioxide, which dissolves readily in ethionic acid, is used as the sulfonating agent, the productivity according to U.S. Pat. No. 3,637,793 is limited by the effectiveness of the cooling system. When contact gas, which is a mixture of dilute sulfur trioxide in inert gases of nitrogen and oxygen, is used as sulfonating agent, productivity is limited not only by the efficiency of cooling system, but also more severely by the contact between incoming dilute sulfur trioxide and ethanol in ethionic acid. If the contact time is not sufficient, sulfur trioxide is not absorbed completely by ethanol in ethionic acid, and part of sulfur trioxide will be discharged from the reaction system along with the inert gases. As a result, the productivity according to this invention is limited.

It is an object of the present invention to overcome the disadvantages of the known processes for the production of ethionic acid, which comprises reacting ethanol and sulfur trioxide in a molar ratio of 1:2 in a falling film reactor at a temperature of 40 to 100° C., preferably between 50 to 75° C., while cooling the reactor with a cooling means. Furthermore, with the use of the process according to the present invention, the yield of ethionic acid is practically quantitative and the quality, i.e., purity and color, of the ethionic acid obtained is excellent.

In comparison with the three methods disclosed in prior arts, the process according to the present invention has the following three advantages: (1) no solvent other than the sulfonation product, i.e., ethionic acid, is introduced into the reaction system; (2) the highly exothermic sulfonation reaction of ethanol with sulfur trioxide is completely controlled; (3) the production capacity can be easily scaled up in a falling film reactor with multi-tube assembly.

The ethanol used in the present process is preferably pure, but can also contain water as in the commercial ethanol-water azeotrope, 95% ethanol. In the case of aqueous ethanol, the water reacts with sulfur trioxide to form sulfuric acid as an impurity in the product of ethionic acid.

The ethanol used in the present process may also be first dissolved in ethionic acid, then reacts with sulfur trioxide in a falling film reactor. Little difference is observed in the products obtained for using ethanol and using an ethionic acid solution of ethanol in the sulfonation process according to the present invention.

The sulfur trioxide used may be pure. To lower the production cost, it is preferable to use the contact gas, which is a mixture of sulfur trioxide and air, obtained in the process for the production of sulfuric acid.

The molar ratio of ethanol to sulfur trioxide is in stoichiometric amount, i.e., for each mole of ethanol, there are used 2 moles of sulfur trioxide. However, slight excess of sulfur trioxide from a molar ratio of 1:2.05 to 1:2.1, is preferably used to ensure a complete conversion of ethanol to ethionic acid. The excess sulfur trioxide will convert ethionic acid to carbyl sulfate, which does not interfere with the subsequent stage to prepare alkali isethionate, alkali vinyl sulfate, and taurine. If an aqueous ethanol is used, additional amount of sulfur dioxide, in an equal molar amount to water content, must be used in addition to the required 1:2 molar amount of ethanol to sulfur trioxide. The byproduct from water, sulfuric acid, is present as an impurity in ethionic acid.

The sulfonation of ethanol with sulfur trioxide is carried out at a temperature from 40 to 100° C., preferably from 50 to 70° C. in a falling film reactor. The falling film reactor can be varied from a single tube to multi-tube assembly, according to the need of production capacity. The cooling means, which is preferably water, has a temperature not exceeding 40° C., especially a temperature in the range of from 20 to 40° C. Lower cooling temperature can also be used if necessary.

In the process according to the present invention, ethionic acid is obtained from the falling film reactor after inert gases are separated from the liquid residue. No further purification is required.

The process according to the present invention may be carried out batchwise, semi-continuously, or continuously, preferably continuously. The reaction is generally performed in a falling film reactor which is cooled by flowing a cooling means at the outside walls of the reactor. At the inner walls of the reactor, ethanol or its solution in ethionic acid flows in downward direction. Sulfur trioxide, diluted with a stream of air or other inert gas, is introduced into the reactor. The concentration of sulfur trioxide generally lies between 2 to 12 percent by volume with respect to the carrier gas.

The following examples will illustrate the practice of this invention but are not intended to limit its scope.

Example 1

The sulfonation of ethanol is carried out in a glass reactor, having a diameter of 0.5 cm and a length of 1 m.

The sulfur trioxide was prepared by reacting sulfur dioxide with oxygen in dry air over a vanadium pentoxide catalyst at about 450° C. The sulfur trioxide in the air is cooled to the inlet temperature in a coil by water. The reactor is cooled by flowing water along the outside of the glass reactor tube. The results are shown in the following table. In all examples, ethionic acid is obtained as a viscous liquid of pale amber color.

TABLE

Reaction Conditions and Results for Sulfonation of 100% Ethanol

| Ex | Feed Rate (mol/hr) | $SO_3$/Feed (mol/mol) | $SO_3$ (vol % in gas) | Temperature (° C.) | Ethionic Acid Yield (%) | Carbyl Sulfate Yield (%) |
|---|---|---|---|---|---|---|
| 1 | 5.0 | 1:2.01 | 5.3 | 50-60 | 98% | |
| 2 | 5.0 | 1:2.08 | 5.3 | 55-65 | 95% | 4% |
| 3 | 5.0 | 1:2.15 | 5.3 | 65-75 | 89% | 11% |
| 4 | 5.0 | 1:2.50 | 5.3 | 75-80 | 50% | 49% |
| 5 | 5.0 | 1:2.01 | 8.7 | 65-75 | 98% | |
| 6 | 5.0 | 1:2.08 | 8.7 | 65-75 | 94% | 5% |
| 7 | 5.0 | 1:2.35 | 8.7 | 70-75 | 65% | 34% |
| 8 | 5.0 | 1:2.60 | 8.7 | 75-80 | 45% | 55% |

Example 2

The sulfonation of 95% ethanol is carried out in a stainless reactor, having a diameter of ½" inch and a length of 48". For 95% ethanol, each mole of ethanol contains 0.134 mole of water, which reacts with equal mole of sulfur trioxide to yield sulfuric acid.

The sulfonation reaction was performed in the same way as described in the previous examples under the following conditions and the results are shown in the following table.

TABLE

Reaction Conditions and Results for Sulfonation of 95% Ethanol

| Ex | Feed Rate (mol/hr) | $SO_3$/Feed (mol/mol) | $SO_3$ (vol % in gas) | Temperature (° C.) | Ethionic Acid Yield (%) | Carbyl Sulfate Yield (%) |
|---|---|---|---|---|---|---|
| 9 | 8.0 | 1:2.14 | 5.3 | 50-60 | 98% | |
| 10 | 8.0 | 1:2.25 | 5.3 | 55-65 | 92% | 7% |
| 11 | 8.0 | 1:2.14 | 8.7 | 65-75 | 98% | |
| 12 | 8.0 | 1:2.15 | 8.7 | 70-80 | 97% | 2% |
| 13 | 8.0 | 1:2.18 | 8.7 | 80-90 | 95% | 4% |

Example 3

The sulfonation of 95% ethanol in ethionic acid is carried out as in Example 2. The concentration of ethanol is 23.75%, water: 1.25%, and ethionic acid: 75.0%. The reaction conditions and results are shown in the following table.

TABLE

Reaction Conditions and Results for Sulfonation of 95% Ethanol in Ethionic Acid

| Ex | Feed Rate (mol/hr) | SO$_3$/Feed (mol/mol) | SO$_3$ (vol % in gas) | Temperature (° C.) | Ethionic Acid Yield (%) | Carbyl Sulfate Yield (%) |
|----|---|---|---|---|---|---|
| 14 | 8.0 | 1:2.14 | 5.3 | 50-60 | 99% | |
| 15 | 8.0 | 1:2.25 | 5.3 | 55-65 | 93% | 6% |
| 16 | 8.0 | 1:2.14 | 8.7 | 65-75 | 98% | |
| 17 | 8.0 | 1:2.16 | 8.7 | 70-80 | 96% | 3% |
| 18 | 8.0 | 1:2.20 | 8.7 | 80-90 | 94% | 4% |

It will be understood that the foregoing examples and explanation are for illustrative purposes only and that, in view of the instant disclosure, various modifications of the present invention will be self-evident to those skilled in the art and are to be included within the spirit and purview of this application and the scope of the appended claims.

What is claimed is:

1. A process for the production of ethionic acid which comprises reacting ethanol in a falling film reactor with sulfur trioxide in a molar ratio of ethanol to sulfur trioxide from 1:2.0 to 1:2.25 while cooling the reactor with a cooling means.

2. The process according to claim 1 wherein the reaction temperature is between 40 to 100° C.

3. The process according to claim 1 wherein ethanol used in the sulfonation is from 85 to 100% and water content is from 0 to 15% in ethanol.

4. The process according to claim 1 wherein ethanol used in the sulfonation may contain methanol, butanone, and isopropanol as denaturants.

5. The process according to claim 1 wherein ethanol is dissolved in ethionic acid to obtain a solution of the concentration from 10% to 75%.

6. The process according to claim 1 wherein sulfur trioxide is pure.

7. The process according to claim 1 wherein sulfur trioxide is diluted to 1% to 12% with air.

8. The process according to claim 1 wherein the falling film reactor is single tube reactor or multi-tube assembly.

* * * * *